United States Patent
Chambers et al.

(10) Patent No.: US 10,874,513 B2
(45) Date of Patent: Dec. 29, 2020

(54) EXPANDABLE FRAMES AND PARAVALVULAR LEAK MITIGATION SYSTEMS FOR IMPLANTABLE PROSTHETIC HEART VALVE DEVICES

(71) Applicant: 4C Medical Technologies, Inc., Brooklyn Park, MN (US)

(72) Inventors: Jeffrey W. Chambers, Maple Grove, MN (US); Steven D. Kruse, Brooklyn Park, MN (US); Saravana B. Kumar, Minnetonka, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 47 days.

(21) Appl. No.: 16/271,970

(22) Filed: Feb. 11, 2019

(65) Prior Publication Data

US 2019/0247191 A1     Aug. 15, 2019

Related U.S. Application Data

(60) Provisional application No. 62/629,403, filed on Feb. 12, 2018.

(51) Int. Cl.
*A61F 2/24* (2006.01)

(52) U.S. Cl.
CPC ............ *A61F 2/2445* (2013.01); *A61F 2/243* (2013.01); *A61F 2/2418* (2013.01);
(Continued)

(58) Field of Classification Search
CPC ................................ A61F 2/24; A61F 2/2418
(Continued)

(56) References Cited

U.S. PATENT DOCUMENTS

2004/0186565 A1   9/2004   Schreck
2010/0168839 A1   7/2010   Braido et al.
(Continued)

FOREIGN PATENT DOCUMENTS

WO   2013/059747   4/2013
WO   2018/213137   11/2018

OTHER PUBLICATIONS

International Search Report and Written Opinion, dated May 1, 2019 for PCT Application No. PCT/US2019/17581, filed Feb. 12, 2019.

(Continued)

*Primary Examiner* — Suzette J Gherbi
(74) *Attorney, Agent, or Firm* — Barnes & Thornburg LLP; Jeffrey R. Stone

(57) ABSTRACT

A collapsible and expandable prosthetic heart valve stent is provided and comprising an outer section, a valve support defining a flow channel therethrough, a transition section configured to smoothly transition the outer section to the valve support. The valve support is disposed within an interior defined by the outer section, with the inflow end of the valve support disposed inside the outer section's interior. In some cases, the outflow end of the valve support is at least partially defined by the transition section. The prosthetic leaflets are disposed on the inner surface of the valve support's flow channel and are located at or above the annulus of the heart chamber. A paravalvular leakage mitigation system is attached to the stent to mitigate retrograde blood flow and/or regurgitation.

25 Claims, 6 Drawing Sheets

(52) U.S. Cl.
CPC .......... *A61F 2/2454* (2013.01); *A61F 2/2415* (2013.01); *A61F 2/2436* (2013.01); *A61F 2210/0014* (2013.01); *A61F 2220/0016* (2013.01); *A61F 2220/0075* (2013.01); *A61F 2230/0071* (2013.01); *A61F 2250/006* (2013.01); *A61F 2250/0069* (2013.01)

(58) Field of Classification Search
USPC .................................................. 623/2.1–2.19
See application file for complete search history.

(56) References Cited

U.S. PATENT DOCUMENTS

| | | | |
|---|---|---|---|
| 2010/0249923 A1 | 9/2010 | Alkhatib et al. | |
| 2016/0242905 A1 | 8/2016 | Chambers | |
| 2018/0325664 A1* | 11/2018 | Gonda | A61F 2/2409 |
| 2019/0099265 A1* | 4/2019 | Braido | A61F 2/2418 |
| 2019/0365538 A1* | 12/2019 | Chambers | A61F 2/2418 |
| 2020/0030088 A1* | 1/2020 | Vidlund | A61L 27/34 |
| 2020/0069423 A1* | 3/2020 | Peterson | A61F 2/2436 |
| 2020/0100897 A1* | 4/2020 | McLean | A61F 2/2412 |
| 2020/0113682 A1* | 4/2020 | Chang | A61F 2/2439 |
| 2020/0129294 A1* | 4/2020 | Hariton | A61F 2/243 |
| 2020/0155306 A1* | 5/2020 | Bonyuet | A61F 2/24 |
| 2020/0163765 A1* | 5/2020 | Christianson | A61F 2/2463 |
| 2020/0179111 A1* | 6/2020 | Vidlund | A61B 17/0401 |

OTHER PUBLICATIONS

International Preliminary Report on Patentability issued in related PCT/US2019/017581, dated Aug. 18, 2020.

* cited by examiner

EXPANDABLE FRAMES AND PARAVALVULAR LEAK MITIGATION SYSTEMS FOR IMPLANTABLE PROSTHETIC HEART VALVE DEVICES

CROSS-REFERENCE TO RELATED APPLICATIONS

This application claims the benefit of U.S. Provisional Application Ser. No. 62/629,403, filed Feb. 12, 2018 and entitled PARAVALVULAR LEAK MITIGATION SYSTEMS AND FEATURES FOR IMPLANTABLE PROSTHETIC MITRAL VALVE DEVICES AND IMPLANTABLE PROSTHETIC TRISCUSPID VALVE DEVICES

STATEMENT REGARDING FEDERALLY SPONSORED RESEARCH OR DEVELOPMENT

Not Applicable

BACKGROUND OF THE INVENTION

Field of the Invention

The invention relates to devices, systems and features for mitigating paravalvular leak and optimizing functional efficiency of the prosthetic heart valve, including prosthetic mitral valve implant and prosthetic tricuspid valve implant. More specifically, mitigation of paravalvular leakage for a prosthetic mitral valve implant is provided.

Description of the Related Art

The human heart comprises four chambers and four heart valves that assist in the forward (antegrade) flow of blood through the heart. The chambers include the left atrium, left ventricle, right atrium and left ventricle. The four heart valves include the mitral valve, the tricuspid valve, the aortic valve and the pulmonary valve. See generally FIG. 1.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of. For example, the mitral valve when working properly provides a one-way valving between the left atrium and the left ventricle, opening to allow antegrade flow from the left atrium to the left ventricle and closing to prevent retrograde flow from the left ventricle into the left atrium. This retrograde flow, when present, is known as mitral regurgitation or mitral valve regurgitation.

FIG. 2 illustrates the relationship between the left atrium, annulus, chordae tendineae and the left ventricle relative to the mitral valve leaflets. As is shown, the upper surface of the annulus forms at least a portion of the floor or lower surface of the left atrial chamber, so that for purposes of description herein, the upper surface of the annulus is defined as marking the lower boundary of the left atrial chamber.

Native heart valves may be, or become, dysfunctional for a variety of reasons and/or conditions including but not limited to disease, trauma, congenital malformations, and aging. These types of conditions may cause the valve structure to fail to close properly resulting in regurgitant retrograde flow of blood from the left ventricle to the left atrium in the case of a mitral valve failure. FIG. 3 illustrates regurgitant blood flow with an exemplary dysfunctional mitral valve.

Mitral valve regurgitation is a specific problem resulting from a dysfunctional mitral valve that allows at least some retrograde blood flow back into the left atrium from the right atrium. In some cases, the dysfunction results from mitral valve leaflet(s) that prolapse up into the left atrial chamber, i.e., above the upper surface of the annulus instead of connecting or coapting to block retrograde flow. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Regurgitation can be a problem with native heart valves generally, including tricuspid, aortic and pulmonary valves as well as mitral valves.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally-adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; and trans septal delivery techniques.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See, e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

In addition, all known prosthetic heart valves are intended for full replacement of the native heart valve. Therefore, these replacement heart valves, and/or anchoring or tethering structures, physically extend out of the left atrial chamber, in the case of mitral valves, and engage the inner annulus and/or valve leaflets, in many cases pinning the native leaflets against the walls of the inner annulus, thereby permanently eliminating all remaining functionality of the native valve and making the patient completely reliant on the replacement valve. In other cases, the anchoring structures extend into the left ventricle and may anchor into the left ventricle wall tissue and/or the sub-annular surface at the top of the left ventricle. Others may comprise a presence in, or engagement with, a pulmonary artery.

Obviously, there will be cases when native valve has lost virtually complete functionality before the interventional implantation procedure. In this case the preferred solution will comprise an implant that does not extent outside of, e.g., the left atrium, and that functions to completely replace the native valve function. However, in many other cases, the native valve remains functional to an extent and may, or may not, continue to lose functionality after the implantation procedure. A preferred solution in this case comprises delivery and implantation of a valve device that will function both as a supplemental or augmentation valve without damaging the native leaflets in order to retain native valve leaflet functionality as long as present, while also being fully capable of replacing the native function of a valve that slowly loses most or all of its functionality post-implantation of the prosthetic valve.

In all cases, including two-chamber solutions, paravalvular leakage (PVL) may develop as a result of insufficient sealing or apposition of the prosthetic valve device and the native chamber tissue, including but not limited to annular sealing. In the case of the exemplary mitral valve, PVL results in a retrograde leak of blood from the left ventricle to the left atrium, reducing the efficiency of the heart. Lack of sealing apposition may occur for several reasons.

For example, patients may have at least some calcification in the heart chamber, particularly in the annular surface which works to reduce compliance of that calcified tissue. This reduced compliance reduces the ability of the tissue and the prosthetic heart valve device to seal together on implantation, leaving gaps between tissue and device. The mitral valve annulus and the tricuspid valve annulus may be affected by calcification, leading to poor sealing apposition with the implanted prosthetic heart valve device and PVL.

Further, as seen in FIG. 2, the annular surface comprises an irregular landscape with commissures and other elevation changes and/or shaping that differ from person to person. Accommodation of these anatomical features, and inter-patient differences for them, by an implanted heart valve device must be sufficient to prevent retrograde PVL.

Certain inventive embodiments described herein are readily applicable to single or two chamber solutions, unless otherwise indicated. Moreover, certain embodiments discussed herein may be applied to preservation and/or replacement of native valve functionality generally, with improved PVL mitigation, and are not, therefore, limited to the mitral valve and may be extended to include devices and methods for treating the tricuspid valve, the aortic valve and/or pulmonary valves.

Various embodiments of the several inventions disclosed herein address these, inter alia, issues.

DETAILED DESCRIPTION OF THE INVENTION

Generally, various embodiments of the present invention are directed to devices and methods for creating optimal apposition of a support structure or stent of a prosthetic heart valve to treat cardiac mitral or tricuspid valve regurgitation, mitigating paravalvular leak and, thereby, optimizing functional efficiency of the prosthetic heart valve.

One exemplary embodiment of a prosthetic heart valve comprises a prosthetic mitral valve that is implanted at or above the level of the native mitral valve for the treatment of mitral valve regurgitation in symptomatic patients. The design of the implant allows it to anchor within the left atrium and obtain acceptable apposition to the left atrial anatomy preventing paravalvular leakage (PVL) around exemplary implanted valve device. Specific design features and attributes of the exemplary implant that may be utilized to mitigate against PVL are discussed in detail below. However, it will be clear to the skilled artisan that various aspects and embodiments of the PVL features described herein are not limited to the exemplary implant device. As discussed above, the various embodiments of the present invention are discussed in the context of a prosthetic mitral valve, but the various inventions discussed herein are applicable to regurgitant heart valves generally, including tricuspid, aortic and pulmonary valves.

Figure 1:
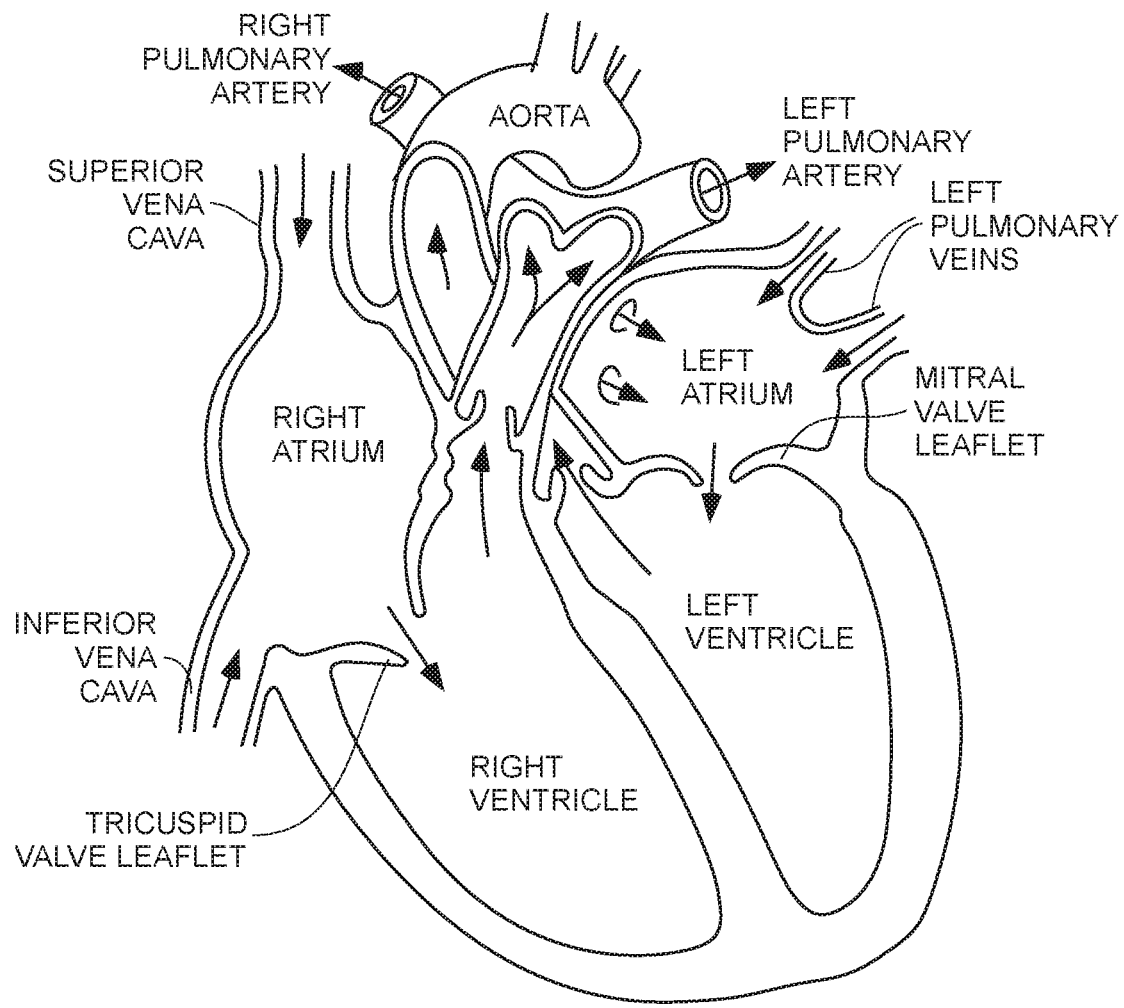
FIG. 1 illustrates certain features of the heart in cross-section.
Figure 2:
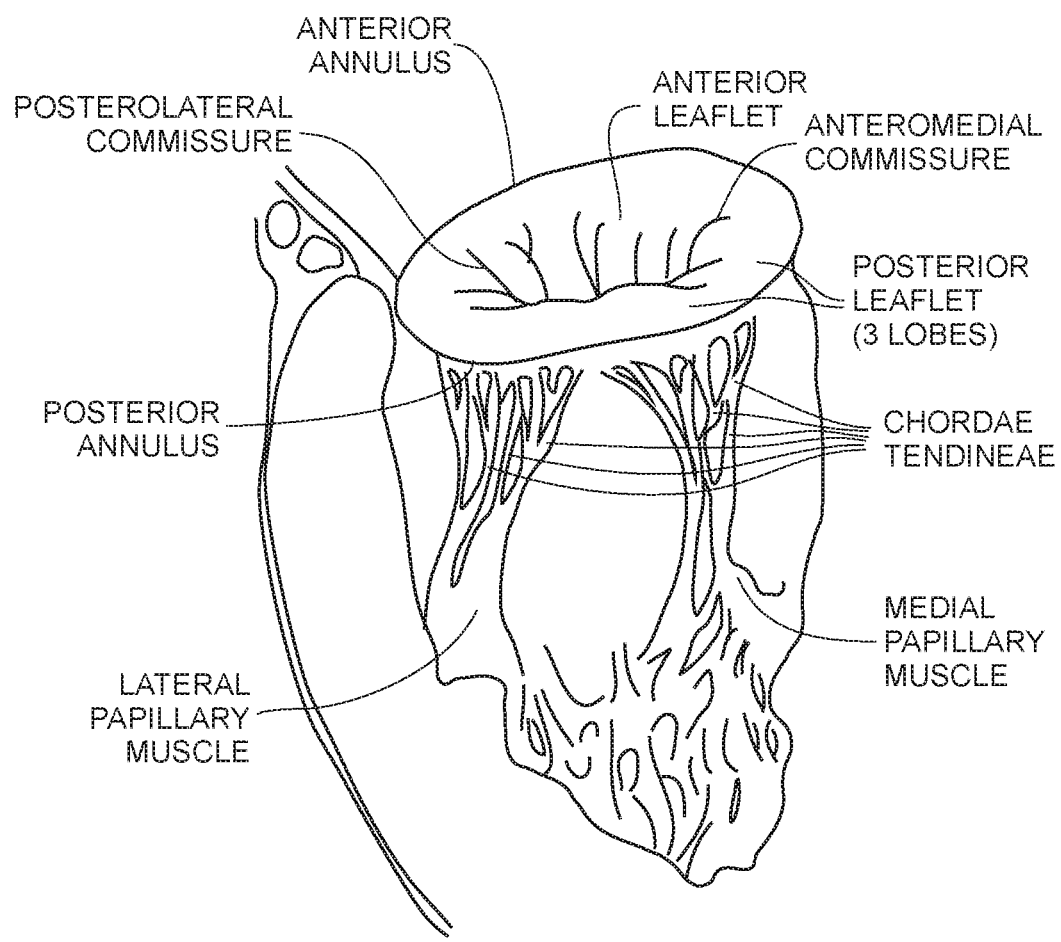
FIG. 2 illustrates a cross-sectional perspective view of the left side of the heart.
Figure 3:
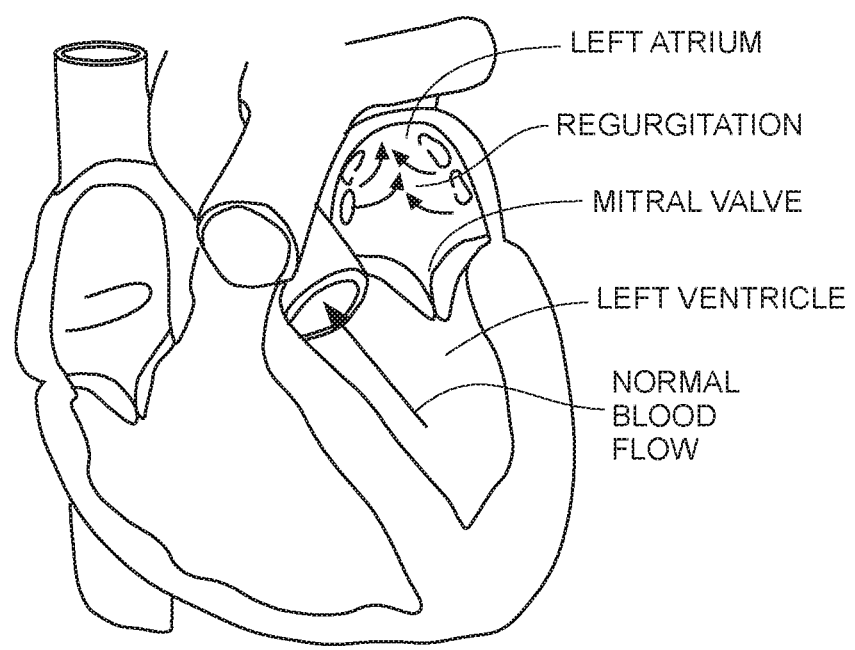
FIG. 3 illustrates a cross-sectional view of the heart showing retrograde blood flow resulting from mitral valve regurgitation compared with normal blood flow.
Figure 4:
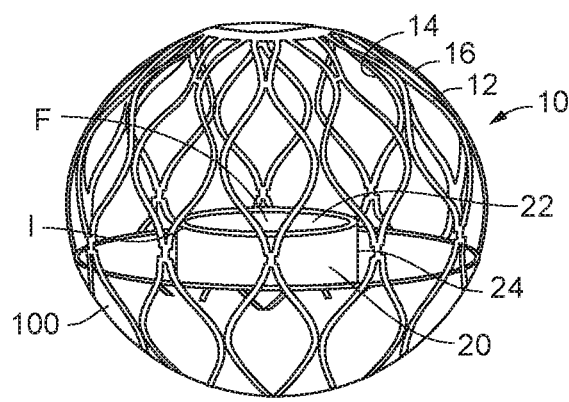
FIG. 4 illustrates a perspective view of one embodiment of the present invention.
Figure 5:
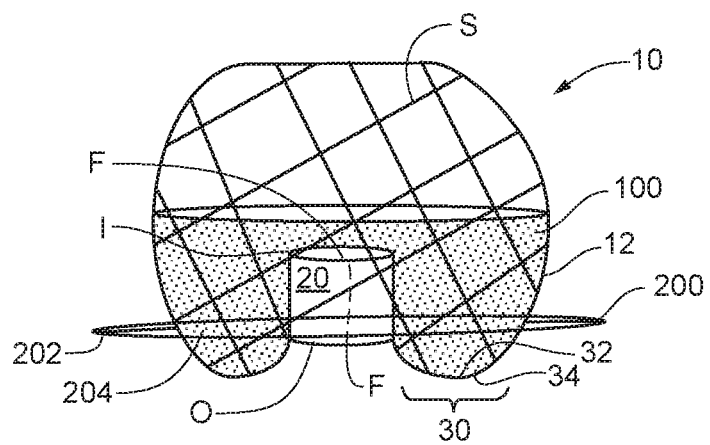
FIG. 5 illustrates a side partial cutaway view of one embodiment of the present invention.

An exemplary prosthetic heart valve device 10 is shown in FIGS. 4 and 5. Device 10 comprises an outer section 12 that has an inner surface 14 and an outer surface 16. A valve support 20 is provided and is operatively engaged and supported by the outer section 12. The valve support 20 comprises an inflow end I, located within the interior of the outer section, and an outflow end O, and an inner surface 22 and an outer surface 24.

The valve support 20 is, in some embodiments formed as a unitary part of the collapsible and expandable stent device 10. Thus, the valve support 20 may be formed by an inward turn in the collapsible and expandable stent cells C, the inward turn occurring across a transition section 30, operatively disposed to transition the device 10 between the outer section 12 and the inner valve support 20. The transition section 30 in this embodiment enables the valve support 20 to be inverted within the interior of the outer section 12. Transition section 30 comprises an inner surface 32 and an outer surface 34. Thus, the inflow end I of the valve support 20 is located radially inside the interior of the outer section 12 and represents a terminal end of the unitary stent device 10. Valve support 20 defines a flow channel F between the inflow and outflow ends I and O, respectively, along the inner surface 22 of the valve support 20. Note that the outflow end O of the valve support 20 may be elevated above (in the upstream or inflow direction) the transition section 30 as shown in FIG. 5, or may be substantially coplanar with the transition section 30. In the case of FIG. 5, the outflow end O of valve support 20 is disposed above the annulus of the exemplary mitral valve. In the embodiment wherein the transition section 30 and outflow end O of valve support are substantially coplanar, the outflow end O of valve support 20 is disposed on the annulus of the exemplary mitral valve. The inner side or surface 14 of the outer section 12, the inner side or surface 32 of the transition section 30, and the outer surface 24 of the valve support 20 all face the interior of the outer section 12. The prosthetic valve leaflets (not shown) may be positioned at any location along the inner surface 22 of valve support 20. Therefore, the prosthetic valve leaflets may be located on or above the annulus of the exemplary mitral valve.

PVL Mitigation System

The design concepts are intended to support minimally invasive procedures for the treatment of valvular regurgitation—mitral, tricuspid and/or otherwise. The stents may be self-expandable (e.g. nitinol or similar materials) or balloon expandable (e.g. cobalt chromium or similar materials). The attachment features described below may be achieved using different materials including fabric, tissue, polymers and other reasonable medical grade materials. The methods of attachment may also vary but not limited to suturing, mechanical attachment features, gluing, coating and other reasonable means of achieving it. Each of the PVL mitigation systems and elements are designed to prevent and/or mitigate retrograde blood flow through the subject heart valve.

Implant Skirt as PVL Mitigation System

The exemplary prosthetic heart device, e.g., prosthetic mitral valve device 10, once implanted is conforming and apposed to the left atrial anatomy. The implant skirt 100 is generally located at the inferior, or outflow, end of the device 10 as shown in FIG. 4. The height of the skirt 100 may be varied to at least partially cover any length of the implanted device 10. The skirt 100 may be positioned either internal or inside the implanted device 10, external or outside the implanted device 10 and/or cover the stent struts S and/or cells formed by the stent struts S. Exemplary skirt 100 location of FIG. 4 shows the skirt 100 attached to the inner surface 14 of outer section 12, inner surface 32 of transition section 30 and outer surface 24 of valve support 20. As noted above, however, the skirt 100 may also be attached to the outer surface 16 of outer section 12, outer surface of transition section 30 and inner surface 22 of valve support 20.

The material of the skirt 100 may be fabric, tissue, and/or other medical grade polymers. The materials may be attached to the device 10 using sutures, glue, adhesives, mechanical fasteners or features, and/or other reasonable methods.

When fabric is used for the skirt 100, the material may be woven, knit, braided, nonwoven and/or hybrid combinations of the listed methods. The tissue used for a skirt 100 may be from bovine, porcine, equine and/or other sources that are adequately processed for human use. The skirt 100 may be constructed out of one material or a combination of materials listed. For example, a combination of tissue and fabric at different locations of the device 100 may be used. One requirement is that the skirt 100 comprise a continuous or unbroken coverage of the area(s) of the device 10 to which skirt 100 is applied to facilitate full unbroken PVL mitigation. This unbroken coverage may be achieved using a single piece of material or may comprise several at least partially overlapping pieces of material.

Material choices are selected depending on porosity to selectively limit diffuse flow and/or redirect the blood flow to the center of the implant (specifically the inner valve support which houses the functioning valve). PVL sealing may be achieved at any level or location of the implanted device 100—preferably at the level of the annulus or above, but may extend below the annulus in certain embodiments. The implant skirt 100 material either fully restricts or only allows diffuse flow through it, thus mitigating against PVL.

FIG. 4 shows one element of a PVL mitigation system comprising a continuous skirt 100 affixed to: the inner side 14 of the outer section 12, the inner surface 32 of the transition section 30 and the outer surface 22 of the valve support 20.

Another embodiment comprises a continuous skirt 100 affixed to: the inner side 14 of the outer section 12, the inner surface 32 of the transition section 30 and the outer surface 22 of the valve support 20. Still another embodiment comprises a continuous skirt 100 affixed to: the inner side 14 of the outer section 12, the inner surface 32 of the transition section 30 and the outer surface 22 of the valve support 20 and/or a second continuous skirt 100 affixed to: the inner side 14 of the outer section 12, the inner surface 32 of the transition section 30 and the outer surface 22 of the valve support 20. Still another embodiment comprises a second skirt 100 affixed to: the outer surface 16 of the outer section 12, the outer surface 34 of the transition section 30 and the inner surface 22 of the valve support 20.

Expandable and Collapsible PVL Mitigation System Features

Specific design features may be further attached to the device 10 to mitigate against PVL at different levels of the implant and, either alone or in combination with the PVL mitigation system comprising at least one skirt 100 as discussed above. Connecting members and features may be added to the device 10 to facilitate PVL mitigation.

Figure 6:
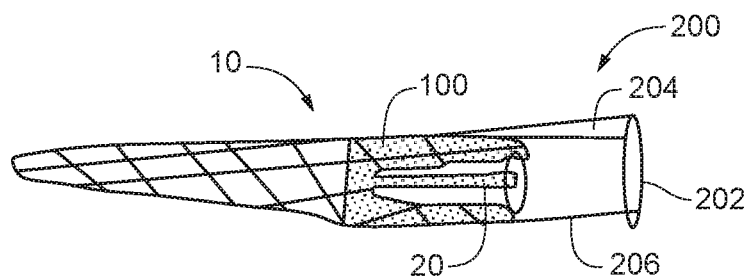
FIG. 6 illustrates a side view of one embodiment of the present invention.

Thus, FIGS. 5 and 7-10 illustrate examples of the device 10 with a fabric or tissue attachment 200 that collapses proximate the inferior end or outflow end O during loading, as is further shown in FIG. 6. This minimizes impact on collapsed implant profile or delivery system profile. The fabric or tissue attachment 200 may comprise a wire frame 202 as in FIGS. 5 and 6 that may be constructed using a self-expandable material (e.g. nitinol) or other such materials that will return to the original preset shape and/or be conformable to the subject heart chamber anatomy. The collapsible wire frame 202 may encapsulate and/or support the fabric and/or tissue material 204 to enable achieving a PVL mitigating seal. The wire frame 202 may expand and collapse in concert with the device 10 collapsing and expanding. Alternatively, a connecting member 206 may be interposed between device 10 and wire frame 202 to facilitate expanding movement of the wire frame 202. Attachments may be added to the connecting member to actively pull back into position once deployed in anatomy. The final geometry of the PVL mitigating feature 200 may be straight or flat (as shown in FIG. 5), or curved (facing cranial or caudal, see FIG. 8). The connecting member 206 may also be attached at any level of the implant—inferior, central or superior—as needed to reduce or eliminate PVL. The connecting member 206 may reside at the inferior or annular side or downstream side of the device 10. The fabric or tissue attachment 200 may curve upwardly or downwardly (see FIG. 8) or fold or coil upon itself (see FIG. 10) to prevent PVL.

Figure 7:
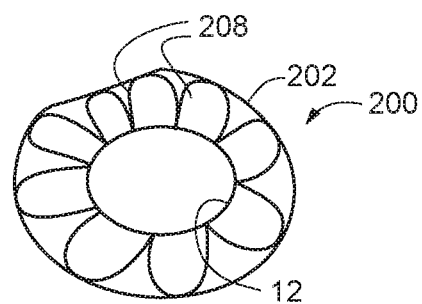
FIG. 7 illustrates a top view of one embodiment of the present invention.
Figure 8:
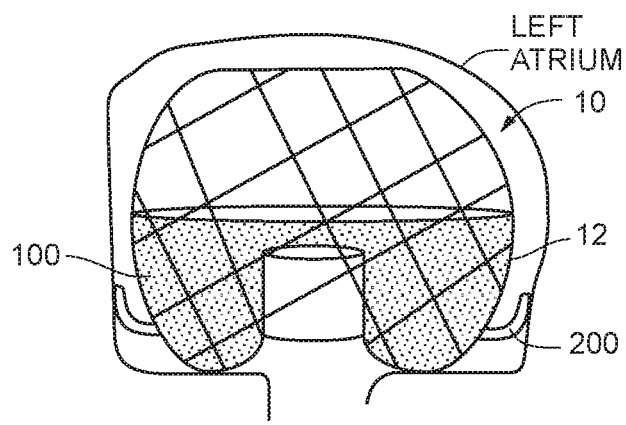
FIG. 8 illustrates a side partial cutaway view of one embodiment of the present invention.

FIG. 7 illustrates one embodiment of the fabric or tissue attachment 200 comprising a wire frame 202 and a series of wire loops 208 connected with the wire frame 202 and with the outer section 12 of device 10. Fabric or tissue 204 is supported by the wire frame 202 and/or wire loops 208, wherein the wire frame 202 and wire loops 208 are adapted and configured to collapse and expand.

The fabric or tissue attachment 200 may also be directly attached to the outer section 12 of device 10 without need of any support connecting member like a wire. When exposed to blood flow in the anatomy, the fabric or tissue attachment 200 may expand (puff) to prevent PVL. The fabric or tissue attachment 200 may be disposed around the circumference of the outer section 12 of device 10 or may be restricted to specific sections thereof. For example, the location of the fabric or tissue attachment 200 may be restricted to the location and/or level that is proximate and/or directly superior to the leaflet commissures of the native valve.

Figure 9:
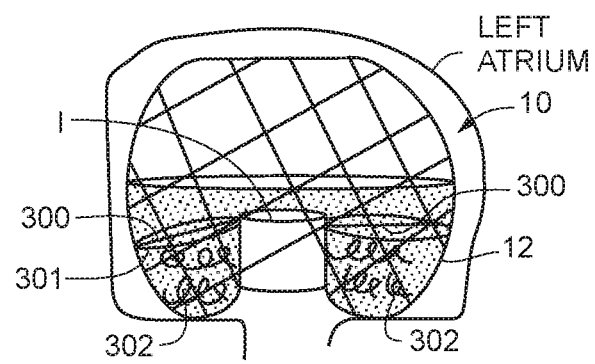
FIG. 9 illustrates a side partial cutaway view of one embodiment of the present invention.
Figure 10:
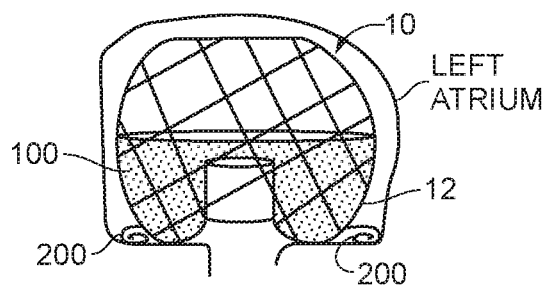
FIG. 10 illustrates a side partial cutaway view of one embodiment of the present invention.

In some embodiments, as shown in FIG. 9, a fabric or tissue cover 300 may extend from the valve support 20 to the outer section 12, the cover 300 located within the interior of the outer section 12, and at least partially surrounding the valve support 12 to provide an at least partial covering thereround. In addition to the covering, an amount of collapsible mesh material 302, such as fabric or tissue or the like may be placed within the covered space created beneath the cover 300 located between the valve support 20 and the outer section 12. In some cases, a wire frame 301 may extend between the valve support to the outer section 12, the wire frame 301 supporting the cover 300.

In certain cases, the angling of the cover 300 between the inner valve support and the outer section may be optimized and positioned to optimize fluid flow into the inflow end I of the valve support 20, for example the cover 300 may be angled downwards towards the inflow end I of valve support 20, wherein the cover 300 is at a higher point at the connection points with the outer section 12 than the connection points of cover 300 with valve support 20. Beyond the optimizing angling of the cover 300, the cover 300 itself may be substantially located and fixed at or near the terminal end of the inner valve support's inflow end I, to encourage fluid flow into the flow channel.

Collapsible Mesh Concept

Figure 11:
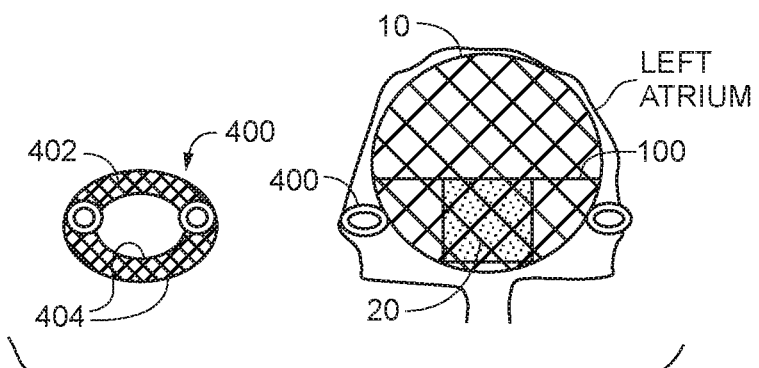
FIG. 11 illustrates a side partial cutaway view of one embodiment of the present invention with a top view of one element broken out.
Figure 12:
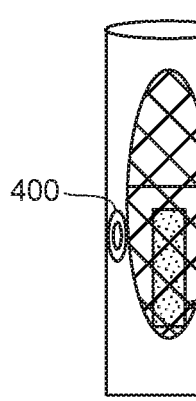
FIG. 12 illustrates a side cutaway and cross-sectional view of one embodiment of the present invention.

The PVL mitigation system 200 (e.g. tissue or fabric) may comprise a mesh frame attachment 400 comprising mesh material 402, e.g., tissue and/or fabric, encapsulated within or attached to a self-expandable mesh frame 404 attached to the outer section 12 of device 10 as shown in FIGS. 11 and 12. The self-expandable mesh frame 404 may comprise a tube with a lumen defined therein. The location of the mesh frame 400 may be at any level of the device 10 (i.e. inferior, central or superior). The mesh 404 may be constructed from nitinol or other such materials. When attached to the inferior end of the outer section 12 of device 10, the mesh 402 may collapse and/or expand separately from the frame of device 10—thus not impacting collapsed implant profile. The mesh frame 404 may also be simply struts that are laser cut into the device's outer section 12. Thus, mesh frame 404 does not need to be a separate attachment but may be included as a laser cut feature to the stent frame and/or outer section 12 of device 10. When deployed from the delivery system, the mesh attachment 400 may simply expand or passively roll into position or actively be manipulated to a specific site in situ. FIG. 12 shows the collapsed device 10 with the mesh frame attachment 400 also in a collapsed configuration within delivery catheter.

Canopy Structure for PVL Mitigation

Figure 13:
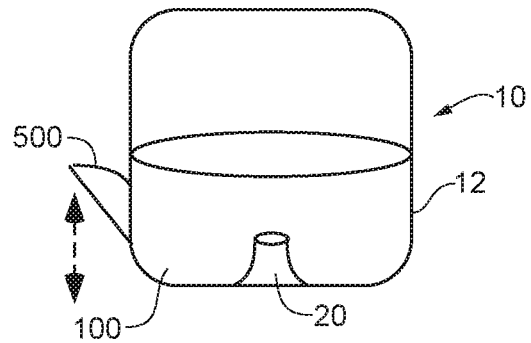
FIG. 13 illustrates a side partial cutaway view of one embodiment of the present invention.

Canopy structures 500—constructed from a combination of tissue alone, fabric alone, a combination of the two with or without attachment members to the outer section 12 of device 10—ay comprise at least a portion of the PVL mitigation system 200 as shown in FIG. 13. When a pressure differential or flow is present, the canopy structure 500 unfurls or unwinds to prevent the flow from entering the left atrium (in case of mitral valve regurgitation treatment). Thus, the canopy 500 is configured to achieve closed and open states, the open state driven by pressure differential and/or regurgitant blood flow. The attachment features, when present, for connecting the canopy structure 500 to the outer section 12 of device 10 may comprise sutures, wires, a continuous fabric or tissue lining. A preferred embodiment of canopy 500 comprises a concave profile to enable unfurling, unwinding and/or expansion during retrograde flow or regurgitation. Thus, in cases where there is no flow or pressure differential due to retrograde flow or regurgitation, the canopy 500 does not inflate or expand. Radiographic materials may be attached to the canopies to help visualize under fluoroscopy or echo usage. The canopies 500 may be distributed evenly or at specific locations of the device 10 and may expand each time retrograde flow or regurgitation is present. Alternatively, once the canopies 500 are expanded, they remain expanded to present a constant barrier to retrograde flow.

The invention claimed is:

1. A collapsible and expandable stent for implanting into at least one chamber of a patient's heart comprising:
   an outer section comprising a stent cell pattern, an outer surface, an inner surface, and defining an interior;
   a valve support comprising a stent cell pattern and extending radially upward into the interior of the outer section, an inflow end and an outflow end, the inflow end extending radially upward into the outer section, the valve support comprising an inner surface defining a flow channel between the inflow and outflow ends, the valve support inverted entirely within the interior of the outer section, wherein the inflow end of the valve support is within the interior of the outer section;
   a plurality of prosthetic valve leaflets disposed within the flow channel defined by the valve support section, wherein prosthetic valve leaflets are configured to allow flow from the inflow end to the outflow end of the flow channel and prevent flow from the outflow end of the flow channel to the inflow end of the flow channel;
a collapsible and expandable transition section comprising a stent cell pattern and configured to transition the outer section to the valve support, wherein the valve support extends radially upward into the interior of the outer section, the transition section comprising an outer surface and an inner surface that faces the interior defined by the outer section, and wherein the transition section turns inwardly to locate the valve support within the interior section,
wherein the outer section, the collapsible and expandable transition section and the valve support comprise a unitary structure, and
wherein the outflow end of the valve support is at least partially defined by the transition section; and
a paravalvular leakage mitigation system affixed to the stent.

2. The stent of claim 1, wherein the outflow end of the valve support does not extend outwardly past the transition section.

3. The stent of claim 1, wherein the outer section, transition section and the valve support comprise a series of uninterrupted stent cells.

4. The stent of claim 1, wherein the paravalvular leakage mitigation system comprises a skirt affixed to: at least a portion of the outer surface of the outer section, the outer surface of the transition section and the inner surface of the valve support.

5. The stent of claim 4, wherein the paravalvular leakage mitigation system further comprises:
a second skirt of material affixed to: at least a portion of the outer side of the outer section, the outer surface of the transition section and the inner surface of the valve support.

6. The stent of claim 3, wherein the paravalvular leakage mitigation system further comprises:
a second skirt affixed to: at least a portion of the inner surface of the outer section, the inner surface of the transition section and the outer surface of the valve support.

7. The stent of claim 1, the paravalvular leakage mitigation system comprising a skirt affixed to: at least a portion of the inner surface of the outer section, the inner surface of the transition section and the outer surface of the valve support.

8. The stent of claim 6, wherein the paravalvular leakage mitigation system further comprises:
a second skirt affixed to: at least a portion of the outer surface of the outer section, the outer surface of the transition section and the inner surface of the valve support.

9. The stent of claim 6, wherein the paravalvular leakage mitigation system further comprises:
a second skirt affixed to: at least a portion of the inner surface of the outer section, the inner surface of the transition section and the outer surface of the valve support.

10. The stent of claim 1, wherein the paravalvular leakage mitigation system further comprises:
a radial extension of the outer section of the stent, extending away from the outer surface of the outer section and at least partially surrounding the outer section.

11. The stent of claim 10, further comprising at least one of the group consisting of: fabric, tissue, mesh material, and a tube comprising a mesh material, attached to the radial extension.

12. The stent of claim 1, wherein the paravalvular leakage mitigation system further comprises:
a collapsible and expandable wire frame attached to the outer section proximate the transition section and extending away from the outer surface of the outer section when expanded, and
fabric and/or tissue supported by the collapsible and expandable wire frame.

13. The stent of claim 1, wherein the paravalvular leakage mitigation system comprises:
a cover comprising fabric or tissue extending between the valve support and the inner surface of the outer section.

14. The stent of claim 13, further comprising:
a collapsible and expandable wire frame attached between the valve support and the outer section, wherein the cover is supported by the collapsible and expandable wire frame.

15. The stent of claim 14, further comprising mesh material disposed in a space defined by the cover, the valve support and the inner surface of the outer section.

16. The stent of claim 1, wherein the paravalvular leakage mitigation system comprises fabric or tissue attached to the outer section and at least partially surrounding the outer surface of the outer section, the fabric or tissue adapted to expand when the stent is expanded.

17. The stent of claim 1, wherein the paravalvular leakage mitigation system comprises fabric or tissue attached to the outer section and at least partially surrounding the outer surface of the outer section, the fabric or tissue adapted to expand when the fabric or tissue is exposed to blood.

18. The stent of claim 16, wherein the expanded fabric or tissue extends away from the outer section.

19. The stent of claim 16, wherein the expanded fabric or tissue is curved.

20. The stent of claim 16, wherein the expanded fabric or tissue is coiled on itself.

21. The stent of claim 1, wherein the paravalvular leakage mitigation system comprises an expandable mesh frame attached to the outer section and at least partially surrounding the outer surface of the outer section, the expandable mesh frame encapsulating a mesh material.

22. The stent of claim 1, wherein the paravalvular leakage mitigation system comprises an expandable mesh tube attached to the outer section and at least partially surrounding the outer surface of the outer section, the expandable mesh tube defining a lumen that is at least partially filled with a mesh material.

23. The stent of claim 1, wherein the paravalvular leakage mitigation system comprises at least one canopy structure defining an interior and moveable between an open state and a closed state, the canopy structure attached to the outer section of the stent and is adapted to move between an open state and a closed state, the canopy structure driven to the open state by retrograde fluid flow or pressure differential.

24. The stent of claim 1, further comprising the stent adapted to supplement and/or replace native valve leaflet functionality.

25. The stent of claim 24, wherein the stent is adapted to supplement and/or replace one or more of the group consisting of: mitral valve leaflet functionality, tricuspid valve leaflet functionality, aortic valve leaflet functionality, and pulmonary valve leaflet functionality.

\* \* \* \* \*